United States Patent [19]

Rice et al.

[11] Patent Number: 4,960,702

[45] Date of Patent: Oct. 2, 1990

[54] METHODS FOR RECOVERY OF TISSUE PLASMINOGEN ACTIVATOR

[75] Inventors: Craig Rice, Alameda; Michael J. Morser; Charles Glaser, both of San Francisco, all of Calif.; Peter A. Donner, Berlin, Fed. Rep. of Germany

[73] Assignee: Codon, South San Francisco, Calif.

[21] Appl. No.: 167,061

[22] Filed: Mar. 11, 1988

Related U.S. Application Data

[63] Continuation-in-part of Ser. No. 76,682, Sep. 6, 1986, abandoned, which is a continuation-in-part of Ser. No. 773,334, Sep. 6, 1985, abandoned.

[30] Foreign Application Priority Data

Sep. 6, 1986 [WO] PCT Int'l Appl. ............. 86/0831

[51] Int. Cl.$^5$ ............... C12N 9/64; A61K 37/547
[52] U.S. Cl. ............................. 435/226; 435/212; 435/219; 435/815; 424/94.64
[58] Field of Search ............ 435/212, 215, 226, 815; 424/94.64; 210/660

[56] References Cited

U.S. PATENT DOCUMENTS

| | | | |
|---|---|---|---|
| 4,245,051 | 1/1981 | Reich et al. | |
| 4,541,952 | 9/1985 | Hosoi et al. | 260/112 R |
| 4,568,544 | 2/1986 | Hasegawa et al. | 424/94 |
| 4,620,948 | 11/1986 | Builder et al. | 530/419 |

FOREIGN PATENT DOCUMENTS 0041766 9/1988 European Pat. Off. .
8401786 5/1984 PCT Int'l Appl. .

OTHER PUBLICATIONS

Einarsson, M., et al., (1985), Biochem. Biophys. Acta 830, 1-10.
Kruithof, et al., Biochem. J., vol. 226; pp. 631-636, (1985).
Rijken et al., J. Biol. Chem., vol. 256, pp. 7035-7041, (1981).
Hoylaerts, et al., J. Biol. Chem., vol. 257, pp. 2912-2919, (1982).

Primary Examiner—Elizabeth C. Weimar
Assistant Examiner—Charles L. Patterson
Attorney, Agent, or Firm—Townsend and Townsend

[57] ABSTRACT

Methods for recovering t-PA from a liquid medium are disclosed. The methods comprise contacting a liquid medium with at least one substrate capable of effecting a separation of intact t-PA from degraded t-PA thereafter recovering the intact t-PA free from other unrelated protein. The present invention also provides compounds produced by this method, compounds comprising intact one-chain t-PA and pharmaceutical compositions containing them and methods for using such compositions.

46 Claims, 4 Drawing Sheets

FIG. 2 PURIFIED TISSUE-PLASMINOGEN ACTIVATOR
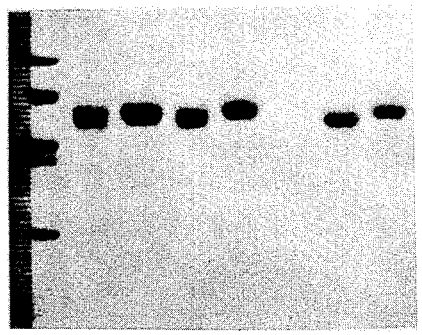
FIG. 3 ZYMOGRAPH: INTACT + DEGRADED T-PA
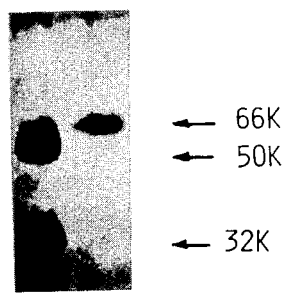
← 66K
← 50K
← 32K
FIG. 4 SEPARATION OF INTACT + DEGRADED T-PA
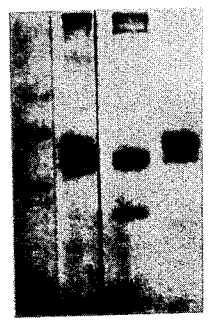

WESTERN BLOT: ONE- AND TWO-CHAIN T-PA
IN CONDITIONED MEDIA 0  1  5  10  50  100   KIU/ML

—ONE-CHAIN

=TWO-CHAIN 0  1  5  10  50  100

=TWO-CHAIN 0  1  5  10  50  100

=TWO-CHAIN

METHODS FOR RECOVERY OF TISSUE PLASMINOGEN ACTIVATOR

RELATED APPLICATIONS

This application is a continuation-in-part of U.S. patent application Ser. No. 076,682, filed Sept. 6, 1986, now abandoned, which was a continuation-in-part of U.S. patent application Ser. No. 773,334, filed on Sept. 6, 1985, now abandoned.

FIELD OF THE INVENTION

This invention relates to the efficient recovery of tissue plasminogen activator (t-PA) from liquid media and more specifically, to improved methods for recovering intact single-chain t-PA substantially free of degraded t-PA and other non-homologous proteins.

BACKGROUND AND PRIOR ART

Plasminogen activators have received attention for their role in the fibrinolytic system. These enzymes catalyze the conversion of the proenzyme plasminogen into the proteolytic enzyme plasmin; plasmin can, in turn, degrade fibrin, a major component of blood clots. Thus, plasminogen activators are potentially useful for the therapeutic treatment of blood clots.

The known plasminogen activators include streptokinase, which is of bacterial origin, urokinase (u-PA), which has been isolated from urine and culture fluids, and tissue plasminogen activator (t-PA), which is available from cultured human cells (Rifkin et al., J. Exp. Med. 139:1317-1328 (1974); Wilson et al, Cancer Res. 40:933-938 (1980)). Streptokinase and u-PA are available commercially, but appear not to possess the therapeutic efficacy of t-PA.

Intact t-PA is a glycoprotein having a molecular weight of about 66,000 daltons, and exists as either a one-chain polypeptide (Binder et al., J. Biol. Chem. 254:1998-2003 (1979)) or it may be cleaved by plasmin (Wallen et al., Prog. in Fibrinolysis 5:16-23, (1981)), into a two-chain form, wherein the two polypeptides are linked by a disulfide bond (Rijken et al., Biochem. Biophys. Acta 580:140-153 (1979)). Non-glycosylated, enzymatically active t-PA has been produced in eukaryotic cells grown in the presence of drugs that prevent glycosylation (Little et al., Biochemistry 23:6191-6196 1984)); and in bacteria (Pennica et al., Nature (London) 301:214-221 (1983)). Degraded forms of t-PA, having molecular weights of approximately 50,000 and 32,000 have been found coexisting with intact, one-chain and two-chain t-PA (Granelli - Piperino & Reich, J. Exp. Med. 148:223-234 (1978)). Prior art methods for isolating t-PA have not been particularly effective at separating the degraded forms of t-PA from the intact t-PA.

In pharmaceutical formulations of t-PA, the availability of substantial quantities of pure intact single-chain enzyme is important and desired. The strong fibrin binding exhibited by t-PA (Thorsen et al., Throm. Diath. Haemorrh. 28:65-74 (1972)) is believed to be important for its therapeutic efficacy. The lower molecular weight degraded forms, which have aberrant fibrin binding properties (Banyai et al., FEBS Lett. 163:37-41 (1983)), do not appear to display the specificity and clot localization properties of intact one-chain and two-chain t-PA. Further, it is believed that single-chain t-PA is more desirable in pharmaceutical formulation than the two-chain form due to the much slower rate at which the single-chain form is inactivated by specific inhibitors of t-PA found in plasma (Lecander et al., Brit. J. Haematol. 57:407-412 (1984)) and due to the potential systemic activation caused by two-chain t-PA. In addition commercially available preparations of t-PA are limited to administration at concentrations at or below 1 mg/ml. For initial administration of t-PA, higher concentrations of t-PA would be preferable.

Various protocols have been described for the purification of t-PA using chromatographic, electrophoretic, and selective extraction and precipitation methods. Most of these methods, including a widely used purification (Rijken and Collen, J. Biol. Chem. 256:7035-7041 (1981)), are not appropriate for the large scale production of t-PA as they are inefficient in product recovery, only partially effective in removing impurities, or use adsorbents which may introduce toxic, mitogenic, tumorogenic or immunogenic ligands into the t-PA preparation (Reagan et al., Throm. Research 40:1-9 1985)). Large scale purification methods employing immunoaffinity chromatography (Wallen et al., Eur. J. Biochem. 132:681-686 1983); Nielsen et al. EMBO J. 2:115-119 (1983)) are limited by the cost of the antibody resin, the difficulty in sterilizing or sanitizing this resin and by the potential for the antibody or fragments of the antibody leaching into the recovered t-PA. In addition, the published methods do not provide procedures to concentrate t-PA to give useful therapeutic formulations. Furthermore, the presence of degraded forms of t-PA in preparations of the purified enzyme remains problematic to those skilled in the art (Kruithof et al., Biochem. J. 226:631-636 (1985)). Degraded t-PA is commonly found in fermentation broth. Degraded t-PA not only dilutes the intact t-PA, but in addition, as mentioned above, it is not specific and is less able to localize clots as the intact t-PA. Therefore, contamination of final t-PA product with degraded t-PA provides serious drawbacks to the product as a therapeutic agent. Large scale chromatographic methods for the specific recovery of intact t-PA free from degraded forms have not been reported. The method disclosed by Rijken and Collen, supra, fails to separate intact t-PA from its degraded forms, and the two forms have consistently co- purified together.

Most tissue culture cells require serum supplementation of media for optimal growth and survival. The known methods for recovery of t-PA from conditioned tissue culture media are generally effective only when serum-free media is used. In those examples wherein serum containing production medium is used (Reagen et al., supra: Cederholm-Williams & Porter, Brit. J. Dermatology 110:423-429 (1984), Kluft et al., Adv. Biotechnol. Processes 2:97-110 (1983)) only partially pure t-PA or t-PA containing degradation products were primarily recovered. This degradation is attributed to serum components and may be only partially blocked by the addition of proteinase inhibitors (Reagen et al., supra). Thus it appears that untreated serum used in growth media for culture cells contains plasminogen and plasmin which are known to proteolytically cleave t-PA (Wallen et al., supra). Adsorbent substrates such as Lysine-Sepharose chromatography have been shown to be effective in the removal of these proteins from serum (Wu et al., Exp. Cell Research 96:37-46 (1975); Quigley et al., J. Biol. Chem. Vol. 249, pg. 4306-4311 (1974)). Such depleted serum is capable of supporting the growth of tissue culture cells Wu et al., supra: Kaufman et al., Molec. Cellular Biology 5:1750-1759 (1985)).

SUMMARY OF THE INVENTION

The present invention provides rapid, efficient methods for the recovery of intact, single-chain t-PA from liquid media e.g., serum-free and serum-supplemented media used to culture cells which secrete intact t-PA or from extracts of cells which intracellularly deposit t-PA or non-glycosylated t-PA polypeptide. The novel methods of the present invention can provide for the recovery of t-PA substantially free of degraded t-PA by contacting a liquid medium with at least one substrate capable of effecting a separation of intact t-PA from degraded t- PA. The phrase "degraded t-PA" refers to species of t-PA fragments that are predominantly 50,000 and 32,000 dalton species, but is not limited to such species and includes and peptide fragment derived from t-PA. Such fragments may retain enzymatic activity.

The present invention also provides methods for further adsorbing t-PA onto additional adsorbent substrates, e.g. adsorbent substrates comprising at least one aminocarboxylic acid, followed by eluting and recovering the t-PA. Such additional adsorption and elution can precede or follow the novel methods, while retaining the benefits of the present invention.

The present invention also provides a method for minimizing the amount of degraded t-PA and two-chain t-PA recovered from serum- or serum fraction-supplemented media by pre-treating the serum with an additional substrate such as, e.g., lysine-Sepharose ™ (Pharmacia Fine Chemicals, Piscataway, N.J.) chromatography. The invention further provides for a novel use of "scrubbed serum" in combination with aprotinin (an inhibitor of t-PA proteases) as an essential reagent if intact single-chain t-PA is to be recovered from serum supplemented media.

One substrate useful in the present invention, $Zn^{++}$ chelate, has previously been employed for recovering t-PA (Rijken et al., supra). However, the prior art protocols differ significantly from those disclosed here. The modified zinc column protocol disclosed here provides the advantages of better separation of intact from degraded t-PA, and increasing the efficiency of purification by separating the bulk of the contaminating proteins, as well as the degraded t-PA, from the desired single-chain t-PA.

The literature inter alia teaches the use of high ionic strength solutions for chromatography, greater than 0.5 M salt concentrations when using metalchelate resins to minimize non-specific adsorption effects. (Rijken et al., supra; Porath et al., Nature 258:598–599 (1975)). The present invention includes the unexpected observation that the use of a low ionic strength washing condition (under 100 mM salt, and preferably NaCl) allows for the elution of degraded t-PA and the majority of other proteins bound to the column while retaining intact t-PA. This results in the ultimate recovery of t-PA free of degraded t-PA and unrelated proteins which is not possible if traditional methods (Rijken et al., supra, Rijken & Collen, supra) are used.

An additional substrate useful in certain embodiments of the present invention, immobilized lysine, has also been used to recover plasminogen activator activity from human plasma and homogenized human venous tissue (Radcliffe and Heinze, Arch. Biochem. Biophys. 189:185–194 (1978)), cadaveric perfusates (Allen and Pepper, Thrombos. Haemostas. 45:43–50 (1981), and from medium conditioned by incubation with a guinea pig tumor cell line (Oerstein et al., Cancer Res. 43:1783–1789)). This substrate, however, has been reported ineffective for the purification of t-PA found in human uterine tissue (Rijken et al., supra).

Previously, the identities of the isolated activators were not rigorously determined, nor were the purities of the enzymes established. Further, the previously reported methods for elution of t-PA from the immobilized lysine substrates did not provide a system to concentrate t-PA. It is important to obtain t-PA in concentrations useful for therapeutic formulation and subsequent administration. The present invention provides a method for recovering t-PA from lysine-Sepharose in a very homogenous, biologically active and pure form, using either basic or acidic eluting conditions. Acidic elution provides a product with higher solubility which is more suitable for pharmaceutical formulation. This formulation provides methods for concentrating the t-PA which include, alone or in combination, dialysis, diafiltration, cationic exchange chromatography on S-Sepharose, and freeze-drying.

The compounds and compositions obtained by practicing the present invention comprise intact t-PA, substantially free from degraded t-PA and other unrelated proteins, as well as methods for using such compounds and compositions. The compositions disclosed herein are in excess of 99% pure intact t-PA.

Specifically the t-PA compositions from this recovery process are unique from previously described recovery processes. The t-PA of this invention is substantially free from two-chain t-PA and degraded t-PA. By "substantially free" it is meant that less than about 10% (w/w) of the total population of t-PA molecules are two-chain or degraded. In addition the t-PA derived from the disclosed recovery processes is substantially in a monomeric form and not aggregated into dimers, trimers, or other multi-meric aggregates. The t-PA compositions described herein are substantially in a nonaggregated form and by "substantially in a nonaggregated form" it is meant that less than or about 1% of the total t-PA molecules present in the composition are in an aggregated form.

In addition the synthetic t-PA described herein is prepared from genetically engineered human cells. These synthetic or recombinant t-PA molecules have a glycoslyation pattern which mimics the glycosylation pattern of naturally occurring t-PA especially as compared to the t-PA products of non-human cells such as hamster, mouse, yeast, insect or bacterial cells.

It should be further noted that the t-PA compositions of this invention as prepared from the disclosed methods embraces both the most common primary amino acid sequences of t-PA found in the human population and other sequences of t-PA having non-critical amino acid substitutions, deletions or additions.

More specifically the disclosed method for recovering intact tissue plasminogen activator (t-PA) from a liquid medium containing intact t-PA and at least one of degraded t-PA and other unrelated proteins comprises the steps of:

(a) contacting said liquid medium with a metal chelate adsorbent substrate selected from divalent cation chelates;

(b) subjecting said metal chelate adsorbent substrate to a first solution which selectively dissociates therefrom degraded t-PA but not said intact t-PA; and (c) subjecting said metal chelate adsorbent of step b to at least one second solution which selectively dissociates therefrom the intact t-PA.

For recovery, it is preferred that the liquid medium comprises intact t-PA at a concentration of .01 to 15.0 mg/ml. The first solution is preferably a solution having a low ionic strength with a salt concentration in the range of 25 millimolar to 100 millimolar and said second solution comprises a high ionic strength solution having a salt concentration in the range of 100 millimolar to 4 molar. The preferred salt is sodium chloride. It is preferred that the second solution of this method comprises a chaotropic agent, preferably urea in a molar concentration from about 0.5 to 3.5 and most preferably 1.0–3.0.

The method disclosed herein also provides for a first and second solutions further comprising at least one disrupting agent capable of selectively disrupting the interaction between said degraded t-PA and said metal chelate adsorbent. The preferred disrupting agent for the first solution comprises about 25–250 mM imidazole with about 25 mM sodium chloride and about 100 mM imidazole being especially preferred.

For the second solution, the preferred disrupting agents are selected from the group comprising imidazole, zinc, sodium ethylenediaminetetraacetic acid and derivatives thereof Especially preferred for the second solution are the disrupting agent, sodium ethylenediaminetetraacetic acid in a concentration of about 10–250 mM and most preferred is a second solution comprising about 1 molar sodium chloride and about 50 mM sodium ethylenediaminetetraacetic acid.

The preferred adsorbent substrate are those substrates comprising an anionic ligand, most preferably a dicarboxylic ligand for chelation with zinc being a preferred metal ion.

A further aspect of this invention is a method of purifying intact tissue plasminogen activator (t-PA) from a liquid medium containing said intact t-PA and at least one of degraded t-PA or other unrelated proteins comprising the steps of:

(a) contacting said liquid medium with a substrate comprising an immobilized aminocarboxylic acid;

(b) subjecting said immobilized aminocarboxylic acid substrate to at least one third solution that dissociates from said substrate degraded t-PA and other unrelated proteins but not said intact t-PA;

(c) subjecting said immobilized aminocarboxylic acid substrate of step b to at least one fourth solution that dissociates from said substrate said intact t-PA. The preferred aminocarboxylic acid is L-lysine.

The third solution is preferably at a neutral pH and the fourth solution is preferably selected from the following group of solutions: (1) solutions having a pH between 8.5–10.5; (2) solutions having a pH between 4.5–3.0; and (3) solutions comprising at least one aminocarboxylic acid. It is preferred that the fourth solutions are at a pH between 4.5–3.0, especially preferred are those acid solutions having a pH between 4.0–3.5. The preferred acids include glycine, aspartate, citrate and glutamate and most preferred is a fourth solution that comprises 10–100 millimolar of an amino acid such as glycine-HCl (30mM) or aspartate (20 mM).

It is specifically disclosed that intact t-PA can be selectively eluted from degraded t-PA and impurities using a third solution that comprises 0.5 molar sodium chloride having a pH of 7.0 to 8.0 and said fourth solution comprises 100 millimolar glycine-HCl at pH 3.0.

This invention also embraces the combination of the two methods described above into a method for recovering intact tissue plasminogen activator (t-PA) from a cell culture medium comprising the steps of:

(a) providing a liquid medium selected from the group of serum-free medium, serum-supplemented medium, serum-fraction supplemented medium and albumin-supplemented medium;

(b) pretreating said serum-supplemented or serum fraction supplemented medium with a first adsorbent substrate capable of removing substantially all plasminogen-like contaminants present in the serum-supplemented or serum-fractions supplemented medium;

(c) adding to said liquid medium a plasmin inhibitor;

(d) contacting said liquid medium with a metal chelate adsorbent substrate selected from divalent cation chelates;

(e) subjecting said metal chelate adsorbent substrate to a first solution which selectively dissociates therefrom degraded t-PA but not said intact t-PA;

(f) subjecting said metal chelate adsorbent of step e to at least one second solution which selectively dissociates therefrom the intact t-PA;

(g) contacting said liquid medium with a substrate comprising an immobilized aminocarboxylic acid;

(h) subjecting said immobilized aminocarboxylic acid substrate to at least one third solution that dissociates from said substrate degraded t-PA but not said intact t-PA; and (i) subjecting said immobilized aminocarboxylic acid substrate of step h to at least one fourth solution that dissociates from said substrate said intact t-PA.

It is a further aspect of this invention that the intact t-PA resulting from the disclosed processes can be concentrated in the presence of non-ionic or zwitterionic detergent with lyophilization in the presence of a stabilizing agent being preferred for concentrating the t-PA. Mannitol is a preferred stabilizing agent.

This invention also relates to the products of the above processes which are biologically active (thrombolytic) and intact t-PA molecules substantially free from degraded t-PA. The disclosed invention embraces intact one-chain t-PA substantially free from two-chain t-PA and degraded t-PA.

More specifically this invention embraces compositions of t-PA in which the percent of the one-chain form of t-PA exceeds 90% (w/w) of the total t-PA. Often in the range of 92-98% one-chain and typically using the disclosed methods 95% of the compositions are in the one-chain form. Using the same methods but increasing the rigor of the serum depletion or by increasing the concentration of serum protease inhibitors, the level of one-chain t-PA can be further decreased until it approximates 100% purity in that no detectable levels of two-chain t-PA are present.

The t-PA is also substantially in a nonaggregated form. More specifically the percent of nonaggregated t-PA ranges from 98.5 to an excess of 99% of the total t-PA present in the described compositions. By optimizing the procedures disclosed herein it is possible to further approximate 100% monomeric form in that there are no detectable aggregates using conventional electrophoretic and chromatographic techniques.

More specifically there is disclosed herein a composition having thrombolytic activity comprising intact t-PA substantially free from degraded t-PA proteins and peptides. By substantially-free it is meant that the composition is homogenous as to biological and biochemical properties and migrates as a single band or peak under standard electrophoretic and chromatographic assay procedures. There are also described herein compositions comprising intact one-chain t-PA substantially free from two-chain t-PA and degraded t-PA and compositions wherein the percent one-chain form of t-PA is about or in excess of 90% (w/w) of the total t-PA.

The t-PA compositions are generally in excess of 650,000 international units per milligram and typically have a specific activity of between or about 700,000 and approximately at or less than 800,000 international units per milligram and are preferably substantially free of detergent. The preferred compositions are preferably in a substantially nonaggregated form. Preferably, the nonaggregated form of t-PA is at least about 99% of the total t-PA, and most preferably in excess of 99.5%.

The most preferred composition is a homogenous composition comprising synthetic t-PA that is characterized by a specific activity above about 700,000 international units per milligram; that is substantially free of detergent; that is composed of one-chain t-PA in excess of about 95% (w/w) of the total t-PA; that is substantially free of non-human proteins and proteins not related to t-PA; that is composed of sialic acid that is less than about 0.5% of the total composition by weight; and that is substantially free of degraded t-PA.

The preferred expression host cells are derived from human melanoma cells, and the preferred t-PA produced by the cells as derived from the described methods has a sialic acid content less than or equal to 1.0% of the total composition by weight. Typically these synthetic t-PA molecules have a content of sialic acid that is often less than 0.75% and typically at approximately 0.5% of the total composition by weight. The synthetic t-PA molecules are substantially if not entirely free from non-human eukaryote proteins.

The preferred final product is a lyophilized powder derived from the above methods essentially comprised of t-PA and glycine-HCl.

This invention also embraces a depleted culture medium able to sustain cells producing t-PA that has been pre-treated to remove plasminogen-like contaminants using the methods described above. Preferred are media capable of sustaining human melanoma cells.

Finally this invention embraces methods of treating a host in need of thrombolytic therapy comprising administering to said host an effective amount of the composition derived from the above methods.

It is thus an object of the present invention to provide a rapid, simple and efficient method for the recovery of tissue plasminogen activators which increases the recovery of intact t-PA, substantially free of degraded t-PA and other undesirable proteins and polypeptides, from a variety of liquid media such as those used in the culture of eukaryotic or bacterial cells, or from extracts of such cells, which express the intact t-PA polypeptide.

It is a further object of the present invention to provide a method which maximizes the amount of single-chain enzyme relative to the amount of two-chain recovered.

It is a further object of the present invention to provide a method for the recovery of intact t-PA substantially free of other proteins including other plasminogen activators, such as u-PA, and non-homologous proteins.

It is yet another object of the present invention to provide a method for the recovery of intact t-PA which provides a product suitable for the subsequent formulation as an effective pharmaceutical composition for therapeutic use.

It is yet another object of the present invention to provide a method for formulating t-PA in a concentration suitable for therapeutic use.

It is yet another object of the present invention to provide a method for formulating t-PA useful for large scale commercial production of the desired form of t-PA.

BRIEF DESCRIPTION OF THE DRAWINGS

FIG. 2 shows an SDS - polyacrylamide gel electrophoresis of tissue plasminogen activator. The figure shows a Coomassie blue stained gel (Laemmli, Nature (London) 227:680–685 (1970)) of three independent preparations of t-PA recovered using the procedures described in Example 1 from conditioned medium supplemented with pre-treated serum. The left most lane contains a mixture of reduced and alkylated standard proteins, from top to bottom: phosphorylase b (94,000 mw), albumin (67,000 mw), ovalbumin (43,000 mw), carbonic anhydrase (30,000 mw). The remaining lanes each contain 5$\mu$g tissue plasminogen activator. Lanes marked with a (+) contain t-PA which had been chemically reduced with DTT before electrophoresis.

FIG. 3 shows a zymograph of t-PA recovered by a method of the present invention from ZN chelate Sepharose. Each lane contains one unit of t-PA. The samples were mixed with Laemmli sample buffer (no DTT), but not heat denatured, and electrophoresed at 4° C. through a 0.75 mm thick 8.7% SDS polyacrylamide gel using the Hoeffer "Mighty Small ™" electrophoresis unit. Electrophoresis was carried out at a constant 150 V. After electrophoresis, the gel was soaked for 15 minutes each in two changes of 100 mls of phosphate buffered saline (PBS), 2.5% (v/v) Triton X-100, followed by two washed with PBS. The gel is placed onto a standard plasminogen-enriched fibrin plate and incubated at 37°. Zones of clearing are detected within 2 hours. Lane "A" was obtained from samples eluted with 20 mM Tris-HCl (pH 7.5), 25 mM NaCl, 0.1 M imidazole, 0.01% Tween 80 (termed Zn A), and indicates more rapidly migrating (i.e., degraded) t-PA near 50,000 and 32,000 daltons. Lane "B" was recovered by elution with 20 mM Tris-HCl (pH 7.5), 1.0 M NaCl, 50 mM NaEDTA, 0.01% Tween 80 (termed Zn B).

FIG. 4 shows the separation of intact and degraded t-PA. The figure shows a coomassie blue stained gel of a non-reduced sample of partially purified t-PA which contained intact (65,000 mw) and degraded (50,000 and 32,000 mw) t-PA ("Load") and samples in which a substantial separation of these forms into the "A pool" ("Zn A"), and "B pool" ("Zn B") had been effected through chromatography on Zn-chelate Sepharose using the protocols described herein. Other experimental details were as described in FIG. 2.

DETAILED DESCRIPTION

Figure 1A:
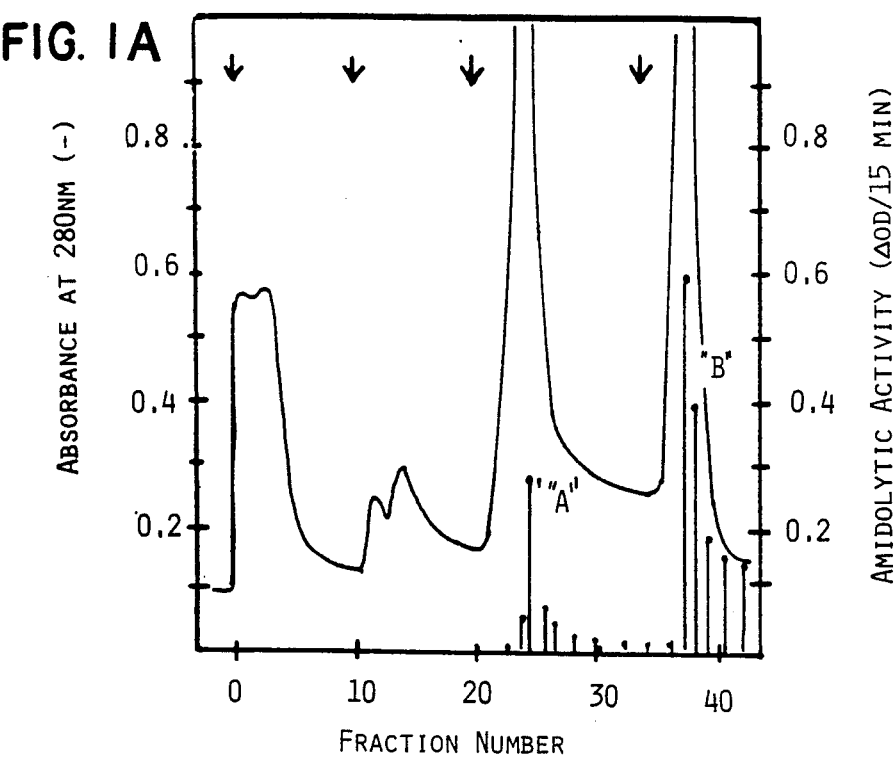
FIG. 1 shows chromatography studies of tissue plasminogen activator. Conditioned serum-free medium or medium supplemented with serum which had been pre-treated by adsorption with lysine-Sepharose was clarified and applied to a column of Zn-chelate Sepharose ™. This column was developed as described in the text of Example 1. FIG. (A) shows the elution pattern of total protein (absorbance at 280 nm) and t-PA activity (histograph). A 5–50 microliter ($\mu$l) aliquot of each fraction was incubated at 37° C. with 200 $\mu$l of 0.01 M Tris-HCI (pH 8.5), 0.1% Tween 80 and 0.2 mM S-2288 ™ (Kabi). The change in adsorbancy at 405 nm was monitored to measure the amidolytic activity of t-PA. The t-PA contained in the "Zn B" fractions was applied to a lysine-Sepharose ™ column, and eluted either at pH 8.0 (FIG. B) or at pH 4.0 (FIG. C) as described in the text of Example 1. In each of the figure panels the arrows at the top indicated the application of a different wash or elution buffers to the columns.

Rapid, efficient procedures have been developed for the recovery of intact, single-chain tissue plasminogen activator (t-PA) from a liquid medium. The methods of the present invention comprise contacting liquid medium which contains t-PA with at least one substrate capable of effecting a separation of intact t-PA from degraded t-PA, and with additional substrates capable of effecting a separation of the intact t-PA from other unrelated proteins.

The present invention also provides methods for treating serum, which is to supplement the nutrient medium used for the production of t-PA by tissue culture cells, by contacting this serum with lysine-Sepharose. This pre-treatment was found to be essential to minimize the proteolytic degradation of t-PA and further effects the removal of serum proteins which otherwise co-purify with t-PA.

The present invention also provides compounds and compositions obtained by practicing the present invention, as well as compounds and compositions comprising intact t-PA, and other unrelated proteins and methods for their use.

A. Media

The media for culturing t-PA producing cells is a non-critical aspect of this invention. There are many different media which have been reported to permit high levels of t-PA to be produced from a variety of different cell sources both naturally occurring and genetically altered by recombinant technology. Any eukaryotic or procaryotic cell culture or cell line which secrets t-PA or non-glycosylated t-PA, such as tunicamycin treated RPMI 7932 cells (Little et al., supra), melanoma cells genetically altered by recombinant technology to produce t-PA or lysates of cells, such as E. coli (Pennica et al., supra), which deposit the t-PA or the non-glycosylated t-PA polypeptide intracellularly, would be appropriate conditioning agents for liquid media useful in the present invention.

The preferred cells for use as conditioning agents are human cells, particularly RPMI 7932 cell-lines that have been genetically engineered to express high levels of t-PA.

A preferred source of t-PA can be obtained by isolating the t-PA gene from an E. coli culture (strain MH-1) on deposit with the American Type Culture Collection (ATCC) in Bethesda, Maryland having Accession No. 67,443. The preferred host cell for expression is a melanoma cell CHL-1 also on deposit with the ATCC having accession No. CRL 9446. Standard cloning techniques are sufficient to obtain the t-PA plasmid and insert it into the appropriate cell line. The methodology used for obtaining conditioned media in the examples provided is described in detail in U.S. patent application Ser. No. 074,083 entitled "Transfected cells containing plasmids having genes oriented in opposing directions and method for obtaining same," which was filed on July 16, 1987 and is incorporated by reference herein.

Briefly the preferred t-PA producing melanoma cells have been selected for the ability to grow to very high densities. In the preferred system use is made of the fact that the CHL-1 cells are adherent and can be cultured on microcarriers for cellular support. The cells in the bioreactor are continually perfused with fresh nutrient media, while the conditioned media is continually removed. The majority of the cells are retained in the reactor. Standard growth conditions are well known. (Eg., Kluft, et al., Adv. Biotechnology Proc. 2:97–110 (1983).

Regardless of the conditioning agent, conditioned liquid media will generally contain a mixture of intact t-PA and degraded t-PA that can be separated using adsorbent substrates. Degraded t-PA includes those forms of t-PA which have been proteolytically cleaved to produce lower molecular weight forms, such as the 50,000 and 32,000 species. Also included are those forms of t-PA which have been modified to alter their fibrin binding or fibrin activation characteristics, resulting in decreased thrombolytic activity or decreased specificity.

The conditioned medium is clarified prior to the first adsorbtion step. Clarification can be achieved by a variety of known methods including centrifugation, filtration or chromatographic techniques. Preferably the medium is clarified by passing through a 2 micron filter. The clarified media is then pH adjusted to between 6.5 and 8.5 and chilled to 4° C.

B. Adsorbinq Substrates

Adsorbing substrates for use in this invention are available in a variety of types and from a variety of commercial sources. These substrates function by having ligands able to effect a separation of intact t-PA from degraded t-PA.

The substrates are comprised of 3 elements: (1) a support substrate; (2) spacer arm; and (3) ligand. The adsorbent substrates are also known as activated resins.

Support substrates can comprise any support materials known to the art which do not interfere with the separations as disclosed herein. Such support substrates can be linked, e.g., covalently bound, to the separation ligands by any conventional means to provide increased ease in handling and washing such substrate to improve the efficiency of the method of the present invention. Support substrates known to the art include dextrans, agarose, cellulose, polyacrylamide, silica, etc. When ligand is linked to a support substrate, the term "resin" is used.

The spacer arm linking the ligand and support substrate is a non-critical factor. It need only effectively separate the ligand and support substrate to avoid interference with the separation of degraded and intact t-PA. Typically the spacer arm is an aliphatic chain of 0-12 carbons, the chain can be substituted with hydroxyls to decrease the hydrophobic properties. Other spacer arms are available on commercially prepared resins.

The preferred ligand is a chelator of divalent metals; a dicarboxylic amine being most preferred. However other ligands such as lysine or mercurial type binders can also be used.

Commercially available adsorbent substrates for use in this invention include ZN++ Chelate Sepharose ™, Tris(carboxylmethyl)ethylenediamineagarose, lysine-sepharose and hydroxymercuribenzoateagarose.

Examples of chelating ligands include an adsorbent substrate comprising the general formula:

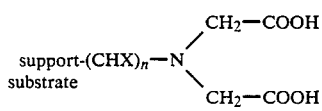

where X is hydrogen or hydroxyl, n is zero to twelve and where n is greater than 1, the substituents represented as X can be the same or different. These molecules chelate metal ions such as Zn++, Cu++ or Co++. Other chelating agents capable of complexing metal ions may be useful in the present invention as well (e.g, iminodisulfides). The columns employing the above adsorbent substrates preferably have a high binding capacity and flow properties such that the t-PA can be rapidly concentrated from the culture medium. Desirably, the medium should be passed through the first column without significant depletion of essential nutrients, modifications of pH or ionic strength nor addition of compounds toxic to tissue culture cells, so that the medium may be recycled into the culture, allowing for rapid separation of t-PA from components that would lead to detrimental alteration upon prolonged contact.

Additional benefits can be obtained in the practice of this invention by employing a plurality of ligands, such as lysine and propylsulfonate to further separate intact t-PA from undesirable contaminants.

C. Pretreatment of Serum for Use in Nutrient Media

Certain preferred embodiments of the present invention produce higher yields of intact one-chain t-PA, substantially free from intact, two-chain t-PA and degraded t-PA. In the preferred embodiment, the liquid medium is serum-free nutrient medium incubated with RPMI 7932 cells or genetically altered melanoma cells. This medium usually contains low levels of degraded t-PA and unrelated proteins in mixture with intact t-PA. However, tissue culture cells frequently require for optimal growth or viability media with serum, fractionated serum, or defined proteins, such as albumin, transferrin, insulin, cell attachment, growth factors, etc. It is reported in the literature (Reagen et al., supra: Cederholms-Williams and Porter, supra: Kluft et al., supra) and observed by us that the presence of serum in the medium used for the production of t-PA results in increased levels of degraded and two-chain t-PA or decreases the purity of the t-PA recovered.

In the preferred embodiment of the present invention where serum or fractionated serum was used to formulate the liquid medium, it was generally pre-treated by adsorption to lysine-Sepharose. This pre-adsorbed serum supported survival and growth of the hamster cell cultures equivalent to untreated serum (Wu et al., supra: Kaufman et al, supra). This pretreatment removed substantially all the plasminogen or plasmin from the serum (Deutsch and Mertz, Science 170:1095–1096 (1970). Plasminogen, when converted to plasmin by plasminogen activators, is known to catalyze the degradation of t-PA (Banvai et al, supra: Wallen et al., Prog. Chem. Fibrinolysis Thrombolysis 5:16–23 (1983)). It was also reported that the inclusion of protease inhibitors in t-PA production medium is only partially effective in preventing the degradation of t-PA (Reagan et al., supra)

Serum is known to contain large amounts of fast acting protease inhibitors. Thus intact t-PA was previously reported to be easily obtained from such media. The invention herein embraces the discovery that standard purification procedures lead to removal of these inhibitors, co-purification of t-PA, plasmin and plasminogen and subsequent degradation of the purified t-PA.

Contrary to the standard techniques, this invention teaches that depletion of serum prior to conditioning is an essential step to obtaining intact one-chain t-PA.

We have furthermore observed that the pre-treatment of serum removes other materials having affinity for lysine, and which may otherwise co-purify with the t-PA in certain embodiments of the present invention. The use of pre- adsorbed serum is therefore essential for the recovery of intact t-PA free of degraded t-PA and other unrelated protein from serum-supplemented medium.

As an example, the pre-treatment of serum was accomplished by first diluting the serum with three volumes of cold sterile water. The diluted serum was passed at 4° C. through a column of lysine-Sepharose resin at a flow rate of about one column volume per hour. The effluent, herein referred to as "scrubbed serum", was collected, assayed for plasminogen (Wu et al., supra), filter sterilized and stored frozen until used in the formulation of the liquid medium. Approximately one milliliter of resin was used to treat each milliliter equivalent of undiluted serum. The level of plasminogen in sera varies significantly. It therefore is sometimes necessary to use amounts of resin greater than that specified above.

With all serum tested, it was found that less resin was required for the complete removal of plasminogen if the serum is diluted as described here, than if undiluted serum is used as described in the literature (Wu et al., supra). It may be necessary with the diluted serum to adjust the osmotic strength by adding NaCl before using it to supplement tissue culture media.

The resin can be regenerated by washing it with a solution comprising 5 M urea, 1 M NaCl, 50 mM Na EDTA (pH 7.5), followed by sterile water. The resin column was sanitized by washing it with 20% ethanol and then storing the column with ethanol for at least 18 hours. The resin was thoroughly washed with sterile water before re-use.

D. Conditioning Media with t-PA Producing Cells

To further exemplify a presently preferred embodiment of one aspect of the present invention, RPMI 7932 cells, adsorbed to tissue culture flasks (Rijken and Collen, supra) or microcarriers (Kluft et al., supra) were used to condition liquid media which contained 0 to 0.5% scrubbed serum.

A protease inhibitor is also added to the scrubbed media. It must be nontoxic to the cells and preferably a serine protease and most preferably a plasmin inhibitor. Examples of useful protease inhibitors are aprotinin, alpha-1 antitrypsin, alpha-2 macroglobulin, and soybean trypsin, inhibitor. Preferred is Aprotinin at a concentration of 5 to 100 KIU/ml, and typically 10 KIU/ml was included in the t-PA production medium.

The t-PA producing cells are allowed to condition the media and then were removed by centrifugation or filtration. Filters used for clarification should be of low-protein binding materials. It is useful to pre-treat the filters by passing a solution of 0.1% Pluronic F-

68 ™ (BASF) or Tween ™ 80 (Atlas Chemical Company, Inc.) therethrough.

Non-ionic detergents are ordinarily used during cell extractions and chromatography to increase t-PA yields and reduce non-specific adsorption. The use of non-ionic detergent such as Tween 80 or Triton X-100 to enhance the recovery of t-PA is well known (Rijken et al., supra). However, since most common non-ionic detergents have critical micellar concentrations on the order of 0.001%, they cannot be effectively removed by simple dialysis, and therefore impede the concentration of solutions. Zwittergent 3-12 works effectively in ensuring high yields of t-PA, and can be used at a concentration of 0.05%, less than one-half of its critical micellar concentrations. Because of its relatively high critical micellar concentration, the detergent can be removed effectively by dialysis or gel filtration using low pH buffers such as those described previously for the third solution used to wash the lysine sepharose column.

Furthermore, columns that can be eluted at low pH, such as lysine sepharose or propyl-sulfonate columns, allow for the recovery of detergent-free t-PA. The detergent-free t-PA can be formulated without detergents or with other desired surfactants (for example, Pluronic F-68) added back, if desired, at concentrations appropriate for intravenous use.

Clarified conditioned media are chilled to approximately 4° C., adjusted to between about pH 7 and 8 with 1 M HCl or NaOH, supplemented with 0.01% (w/v) Tween 80 or Pluronic F-68 and passed through a first column comprising $Zn^{++}$ Chelate Sepharose ™ or $Zn^{++}$ Chelate Fast Flow ™ resin. These resins were prepared as recommended by the manufacturer.

Routinely, the t-PA from 200 liter of 0.5% serum supplemented conditioned medium can be completely adsorbed onto 1 liter of resin. Medium may be passed over the resin at the maximal flow rate recommended by the manufacturer, with substantially all the detectable t-PA activity retained on the resin.

Optimal binding and recovery of t-PA was achieved when chromatography was performed at 4° C. using buffers of approximately pH 7-8, e.g., 20 mM Tris-HCl (pH 7.5 measured at 20° C.), and supplemented with 10 KIU aprotinin/ml and with 0.01% (w/v) Tween 80 or Pluronic F-68.

The t-PA-charged resin was washed with buffer containing approximately 1.0 M NaCl to remove non-specifically adsorbed material, and then with a buffer containing approximately 25 mM NaCl to decrease the ionic strength of the aqueous phase of the resin. This first eluting buffer is also referred to as the "first solution."

Plasminogen activators which have been adsorbed during the practice of the present invention can be eluted from the substrate. When employing an adsorbent substrate, an agent which is capable of disrupting the adsorption will be useful. It is considered desirable to elute t-PA or other proteins by means of an agent which competes for the binding sites on the adsorbent. For example, t-PA adsorbed to an adsorbent substrate comprising a metal chelate such as zinc chelate can be eluted with imidazole, histidine or zinc, among others. Elution can also be effected by such means as salt concentration, pH, or the use of chelating agents such as sodium ethylenediaminetetraacetic acid (NaEDTA). The selection of the eluting agent and precise conditions, i.e., pH, ionic strength, temperature, are chosen so that the selective elution of degraded and intact t-PA are achieved thereby.

The decreased ionic strength of the aqueous phase of the intermediate washes, generally less than the equivalent of 100 mM NaCl, and desirably at or below 25 mM NaCl, is an important feature of embodiments of the present invention employing metal chelate adsorbent substrates such as $Zn^{++}$ chelate. The prior art teaches the use of high ionic strength solutions to minimize non-specific ionic interactions of proteins with metal chelating resins. We have surprisingly found that the resolution of this resin is greatly enhanced by the use low ionic strength solutions of less than 100 mM NaCl or similar salts. At these relatively low ionic strengths, degraded t-PA and the bulk of unrelated proteins adsorbed to the $Zn^{++}$ chelate resin can be eluted while retaining most of the intact t-PA adsorbed to the resin. This allows for the final recovery of t-PA essentially free of degraded t-PA and for the production of t-PA of greater purity than is possible had the method for chromatography of t-PA on $Zn^{++}$-chelate resin in the prior art been used. (Rijken et al., supra; Rijken & Collen, supra).

Complete elution of the adsorbed intact t-PA free of the degraded t-PA is achieved by washing the resin with an eluting buffer (second solution) with a high ionic strength and a disrupting agent. The preferred elution buffer contains 1 M NaCl and 50 mM Na EDTA. Alternatively, the eluting buffer can contain 1.0 M NaCl, 100 mM imidazole or gradually increasing amounts of NaCl (0.025 to 1.0 M NaCl) with 100 mM imidazole. The latter results in the successive elution of t-PA subpopulations, distinguished by their differing affinities for the resin under the conditions of increasing ionic strength. In a preferred embodiment, NaEDTA effects the highest recovery of t-PA from the adsorbent substrate.

It is preferred that this first separation take place using a second solution or eluting buffer containing a chaotropic agent such as urea, potassium thiocyanate, guanadine HCl, potassium iodate, or sodium iodide. The precise concentration varies in accordance with the ability of the chaotropic agent to disrupt hydrogen bonds. For the preferred agent, urea the preferred concentration is between about .5 and 3.5 mole per liter of solution. Under the buffer conditions described in the reported literature, the recovery of t-PA from adsorbtion column chromatography was limited to approximately 100 mg per liter of resin. In the presence of urea, the recovery of t-PA per liter of resin can exceed 10 gm per liter of resin and offer recoveries under commercially favorable conditions that approximate 100%. The presence of urea permits for a greater concentration of t-PA to be eluted from the column. The urea concentration is preferably maintained during subsequent purification steps allowing for the handling of t-PA at commercially favorable concentrations (1-10 mg/ml or greater).

The nature of the early eluting components were analyzed. The material eluted from the resin with 25 mM NaCl comprising an additional agent capable of disrupting the adsorption of these species, e.g., 100 mM imidazole, demonstrated plasminogen activator activity and had molecular weights of approximately 50,000 and 32,000. The activity and molecular weights were determined by zymography (Granelli-Piperino & Reich, supra), using plasminogen-containing fibrin indicator plates.

These plasminogen activators could be specifically inhibited and immunoprecipitated by monoclonal antibodies directed against t-PA and therefore appear to be degraded t-PA. Urokinase-PA is also eluted from the resin by this procedure. Since many tissue culture cells secrete u-PA, this chromatography procedure ensures the recovery of t-PA free from this plasminogen activator which possess less fibrin-clot specificity.

E. The Use of a Secondary Adsorbent Column

The intact t-PA recovered from the $Zn^{++}$ chelate resin can be further treated to remove additional, unrelated contaminants. For example, the intact t-PA recovered from the $Zn^{++}$ chelate resin can be passed through a second column comprising an aminocarboxylic acid linked directly or via a spacer (e.g. a six carbon aliphatic spacer) to a support substrate (e.g. Sepharose). The specific aminocarboxylic acid is not critical. The benefits of the present invention can be obtained with any compound wherein both an amino and carboxyl group are free to interact with t-PA.

Lysine is the preferred aminocarboxylic acid. Alternative compounds include, e.g., 3-amino-n-proprionic acid, 4-amino-n-butyric acid, 5-amino-n-heptanoic acid, 6-amino-n-hexanoic acid, among others. Included also are cyclic compounds such as transexamic acid, and other analogs of lysine, such as aminoethylcysteine, lysopine and octopine, which may possess affinity for t-PA. Such compounds also desirably possess a reactive side chain, through which the molecule can be coupled to the support matrix.

When using additional adsorbent substrate in the practice of the present invention, the benefits of the invention are retained independent of the order in which the adsorbent substrates are employed. While the experimental examples necessarily disclose a certain order, it will be readily understood that no limitation is expressed or implied thereby.

In those embodiments wherein a second adsorbent substrate comprising lysine was employed, the t-PA solution containing approximately 1.0 M NaCl obtained from the $Zn^{++}$ chelate resin was diluted ten-fold with 25 mM Tris-HCl (pH 7.5), 0.1% Tween 80 or Pluronic F-68 and 10 KIU aprotinin/ml and passed over L-lysine-Sepharose resin at 4° C. at a rate of approximately two column volumes per hour. In these embodiments, it was discovered that diluting the t-PA with buffer containing 0.1% detergent resulted in greater recovery of t-PA than if the solution had been diluted with buffer containing only 0.01% of the detergent.

The binding efficiency of t-PA to the resin is in part dependent upon the temperature, pH and salt concentration of the medium to be contacted. The binding capacity of the resin was increased with decreasing temperature. The optimal binding of t-PA to the resin occurs at pH 7 to 8, and when the ionic strength of the medium is equivalent to approximately 100 mM NaCl. Dilution, dialyses or gel filtration can be used to modify the ionic strength of the liquid medium to obtain the optimum benefits of the present invention. To ensure optimal binding of t-PA, approximately 1 liter of resin is used for each 10 g of t-PA when chaotropic agents such as urea are present. If conditioned tissue culture medium is directly contacted with the adsorbent, the optimal dilution is approximately one part medium to three parts 20 mM Tris-HCl, 0.1 Tween 80.

The lysine-Sepharose with bound t-PA was washed with a buffer (third solution) to remove unrelated non-t-PA proteins. Typically this third solution is at a neutral pH using any of several common buffers such as Tris-HCl or phosphate salts and at an ionic strength of less than .5 moles of salt. A preferred third solution is 20 mM Tris-HCl pH 7.5, 0.01% Tween 80, Pluronic F-68, or 0.05% Zwittergent 3-12 and 500 mM NaCl. If acid elution buffers are anticipated, it is desirable to prewash the column after the third solution with a detergent free solution of similar composition.

Thereafter the t-PA is eluted with a variant of the third solution referred to as a "fourth solution." The fourth solution may differ by having a pH between 8.5 and 10.5 or it may be at the same neutral pH but contain an eluting agent able to compete with binding sites between the t-PA and the column or it may be an acidic buffer having a pH between 4.0 and 3.0 most preferably an amino acid such as glycine, aspartate, or glutamate but organic acids such as citrate are also useful. At neutral pH, eluting solutions contain eluting agents which are typically zwitterions of suitable size and charge intensity to effect the desired separation. Examples include both aminocarboxylic acids and aminosulfates. Specific examples include 20–30 mM 6-amino-n-hexanoic acid, 20–50 mM L-lysine or 100–300 mM L-arginine.

It should be recalled that the use of chaotropic agents such as urea to stabilize the t-PA when recovered at high concentrations is recommended when elution occurs under neutral of basic conditions. The urea is removed by gel filtration or ultrafiltration with buffer exchange to obtain a composition suitable for pharmaceutical uses.

Specifically, the lysine-Sepharose with bound t-PA describe is first washed with a buffer at pH 7.5 consisting of 20 mM Tris, 500 mM NaCl and 0.01% Pluronic F-68 and optionally followed by a second washing buffer of pH 8.0 (for example, 3 mM Na glutamate containing 160 mM NaCl, 0.01% Pluronic F-68). The bound t-PA can then be eluted by washing the resin with a buffer of pH 4.0 (for example, 3 mM Na-glutamate containing 160 mM NaCl and 0.01% Pluronic F-68).

F. Pharmaceutical Formulations

It is also considered desirable to use an elution procedure that will facilitate subsequent formulation of the t-PA for storage and therapeutic use.

The solution from the lysine-Sepharose column containing the intact t-PA can be directly concentrated, for example, by pressure dialysis using an Amicon pressure dialysis cell with a YM30 membrane (Amicon) or with an analogous membrane in cross-flow apparatus. Using this system at pH 4 it is possible to concentrate t-PA to greater than 1 mg/ml in the absence of urea. It is important that the pH be maintained relatively acidic to effect concentration. It has surprisingly been found that t-PA becomes insoluble at concentrations of 0.1 mg/ml or greater if the pH exceeds 5.0 in the absence of chaotropic agents.

Stabilizing agents are useful in preparing stable preparations. These agents are osmolaritycryoprotectants such as dextrose, mannose and mannitol. Mannitol is preferred.

After concentration to 5 mg/ml of mannitol can be added to the purified t-PA. This solution can be lyophilized and reconstituted by the addition of water without any loss of activity. In a buffer containing 0.1 Pluronic F-68, 160 mM NaCl and 3 mM Na glutamate (pH 4.0), the t-PA activity is stable for at least 7 days at 23° C. and indefinitely when frozen. The t-PA formulated in this manner was shown to actively mediate the lysis of blood clots when administered in vivo.

Cation exchange chromatography can also be used to concentrate the t-PA. The t-PA eluted from the lysine column at pH 4.0 can be directly passed through a column of S-Sepharose-FF ™ (Pharmacia, Inc.) equilibrated at 4° C. with the same lysine column elution buffer. The t-PA is then eluted at pH 5.0 (3 mM Na-glutamate or 2.5 mM Na citrate, 0.01% Pluronic F-68 containing 200-500 mM NaCl).

Compounds of the present invention, prepared as disclosed, are shown to have the capability of recognizing and binding to fibrin, which is present in a host's circulatory system at locations of thromboses. These compounds are also shown to have fibrinolytic activity and, therefore, display thrombolytic activity as well. Preparations of t-PA produced by the methods of the present invention are an improvement over t-PA prepared by other procedures in that the enzyme will be consistently and substantially pure one-chain, substantially free of degradation products and can be concentrated and formulated in solutions for therapeutic uses. The methods of the present invention will result in substantially less contamination of the product with elements of the chromatographic resins likely to be antigenic or tumorigenic. The absence of degradation products from these preparations provides a thrombolytic agent being substantially homogeneous, intact, and monomeric and having greater specificity and less systematic activation of plasminogen.

Compounds of the present invention which are shown to have the above recited physiological effects can find use in numerous therapeutical applications such as, e.g., dissolving blood clots. Thus, these compounds can find use as therapeutic agents in the treatment of various circulatory disorders, such as, for example, coronary or pulmonary embolism, stroke and decreased peripheral blood flow.

These compounds can be administered to mammals for veterinary use such as with domestic animals, and clinical use in humans in a manner similar to other therapeutic agents, that is, in a physiologically acceptable carrier. In therapy dependent on t-PA, it may be important to achieve high plasma levels of t-PA very rapidly by injection. In such cases it will be necessary to have t-PA available in solutions of appropriate concentrations in excess of 1 mg/ml up to a concentration which exceeds 10 mg/ml. Physiologically acceptable carriers or methods for maintaining t-PA in solution at concentrations in this range have not been known prior to the present invention. In general, the administered dosage will range from about 0.01 to 100 mg/kg, and more usually 0.1 to 10 mg/kg of the host body weight. Alternatively, dosages within these ranges can be administered by constant infusion over an extended period of time, usually exceeding one hour, until the desired therapeutic benefits have been obtained.

These compounds can be administered neat, as mixtures with other physiologically acceptable active or inactive materials, or with physiologically suitable carriers such as, for example, water or normal saline. The compounds can be administered parenterally, for example, by injection. Injection can be subcutaneous, intravenous, or by intramuscular injection. These compounds are desirably administered in pharmaceutically effective amounts and often as pharmacologically acceptable salts such as acid addition salts. Such salts can include, e.g., hydrochloride, hydrobromide, phosphate, sulphate, acetate, benzoate, malate, citrate, glycine glutamate, aspartate among others.

A preferred pharmaceutical formulation comprises a glycine, citrate or aspartate (sodium salt) at a concentration of 10-40 mM and a pH range of 2.5-5.0. Optionally containing approximately 4% mannitol to stabilize the solution. Such a formulation has the advantage of maintaining t-PA in a concentration that exceeds 1 mg/ml in that it may reach a concentration of atleast 5 mg/ml and remain soluble. The relatively low pH allows for a stable solution of t-PA in the absence of detergents. Detergent-free formulations of t-PA are a preferred embodiment of this invention.

Moreover such a concentration permits administration to a patient of an initial bolus of 3-5cc having 15-25 mg of t-PA rather than the 6-10cc bolus at 1 mg/ml recommended for the currently available preparations of t-PA (eg. Activase ™) which are prepared in an arginine buffer at a maximum concentration of 1 mg/ml.

Compounds of the present invention can also be used for preparing antisera for use in immunoassays employing labelled reagents, usually antibodies. These compounds and immunologic reagents may be labelled with a variety of labels such as chromophores, fluorophores, such as fluorescein or rhodamine, or radioisotopes such as $^{125}I$, $^{35}S$, $^{14}C$, or $^{3}H$, or magnetized particles, by means well known in the art. These labelled compounds and reagents, or labelled reagents capable or recognizing and specifically binding to them, can find use as, e.g., diagnostic reagents. Samples derived from biological specimens can be assayed for the presence or amount of substances having a common antigenic determinant with compounds of the present invention.

In addition, monoclonal antibodies can be prepared by methods known in the art, which antibodies can find therapeutic use, e.g., to neutralize overproduction of immunologically related compounds in vivo.

In addition, the t-PA as prepared in this invention when suitably labelled with radioisotopes such as $^{131}I$, $^{123}I$, $^{111}In$, or $^{99m}Tc$ may prove useful for the detection and localization of thrombi in patients. (U.S. Pat. No. 4,663,146 which is incorporated by reference herein.)

The following examples are provided by way of illustration, rather than implying any limitation of the subject invention.

EXPERIMENTAL

EXAMPLE I:

Purification of t-PA from Conditioned Liquid Medium.

Liquid medium (1:1 mixture Ham's F-12 and DMEM) containing 0.5% fetal bovine serum, which had been pre-adsorbed with lysine-Sepharose, and 20 KIU aprotinin per ml was conditioned by incubation with RPMI 7932 cells (Rijken and Collen, supra: Kluft et al., supra), or alternatively, other plasminogen activator producing cells. The preferred method of production utilizes the t-PA expression vector inserted in E. coli culture ATCC Accession No. 67,443 and the melanoma cells CHL-1 also on deposit with the ATCC having accession No. CRL 9446. Standard cloning techniques are used and growth conditions are as previously described.

The conditioned liquid medium is clarified by centrifugation at 10,000 × g for 30 minutes at 4° C. or by filtration through low-protein binding membranes (e.g., Gelman Acrodisc 50A) or filter cartridges (e.g., Sartorius, type CA or PH). With the cartridge filters it is considered desirable to pretreat the membranes by prewetting with a solution of 0.1% Tween 80 or Pluronic F-68 to decrease the adsorption of t-PA to the membranes.

Clarified medium is adjusted to approximately pH 7.2 to 7.4 with NaOH, chilled to 4° C., and passed through a chelating Sepharose column complexed with $Zn^{++}$ as recommended by the manufacturer (Pharmacia, Inc.). The column had been previously equilibrated with phosphate buffered saline. Up to 200 equivalent column volumes of medium are passed through the resin at rates up to 50 cm/hr for a 10 cm bed of Sepharose-FF; and greater than 95% of the t-PA activity is bound to the resin. The column is washed at a rate of 50 cm/hr with 20 mM Tris-HCl, 1.0 M NaCl, 0.01% Tween 80, 10 KIU aprotinin per ml until the absorbance (280 nm) of the eluent buffer was equal to that of the applied buffer. The column is then washed with two to three column volumes of 20 mM Tris-HCl (pH 7.5), 25 mM NaCl, 0.01% Tween 80, 10 KIU aprotinin per ml. The t-PA activity associated with the degraded forms of the enzyme is eluted with 20 mM Tris-HCl (pH 7.5), 25 mM NaCl, 0.1 M imidazole, 0.01% Tween 80 (termed eluate "Zn A"). The intact t-PA is recovered by passing 20 mM Tris-HCl (pH 7.5), 1.0 M NaCl, 50 mM Na EDTA, 0.01% Tween 80 through the resin (termed "Zn B"). A typical elution profile is shown in FIG. 1A. Fractions, typically ¼ column volume, are collected and aliquots assayed for t-PA activity using appropriate methods. The t-PA containing fractions of the "Zn B" elution are collected, diluted ten fold with cold 20 mM Tris-HCl (pH 7.5), 0.1% Tween 80, 10 KIU aprotinin per ml and loaded at a rate of 25 cm per hour onto a 20 cm high bed of lysine-Sepharose. A column is chosen such that approximately 1 liter of resin is available for each 0.2 g of t-PA.

The lysine-Sepharose is washed at 4° C. with one column volume of 20 mM Tris-HCl (pH 7.5), 100 mM NaCl, 0.1% Tween 80, 10 KUY aprotinin per ml at a rate of about 25 cm per hour. The column is then washed with 20 mM Tris-HCl (pH 7.5), 500 mM NaCl, 0.05% Zwittergent 3-12, 10 KIU aprotinin per ml until the absorbance of the eluent buffer is equal to the applied buffer.

Figure 1B:
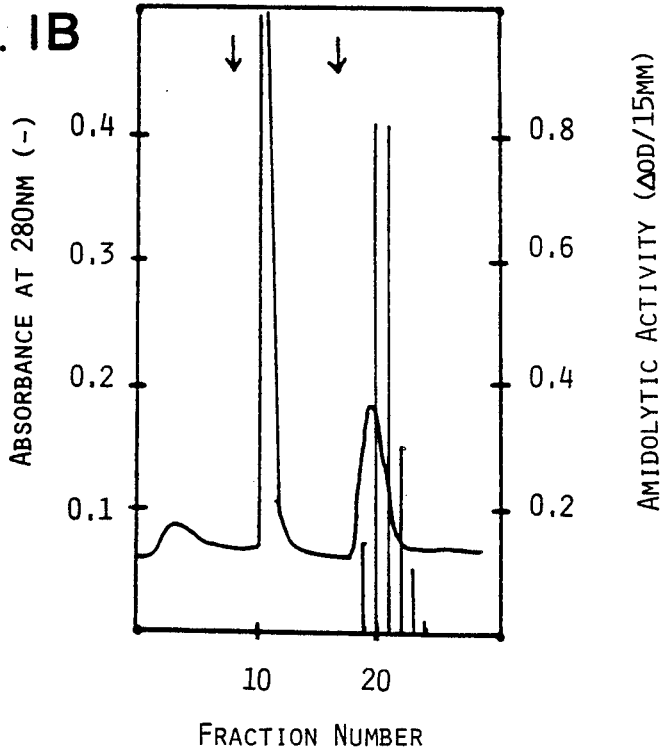
Figure 1C:
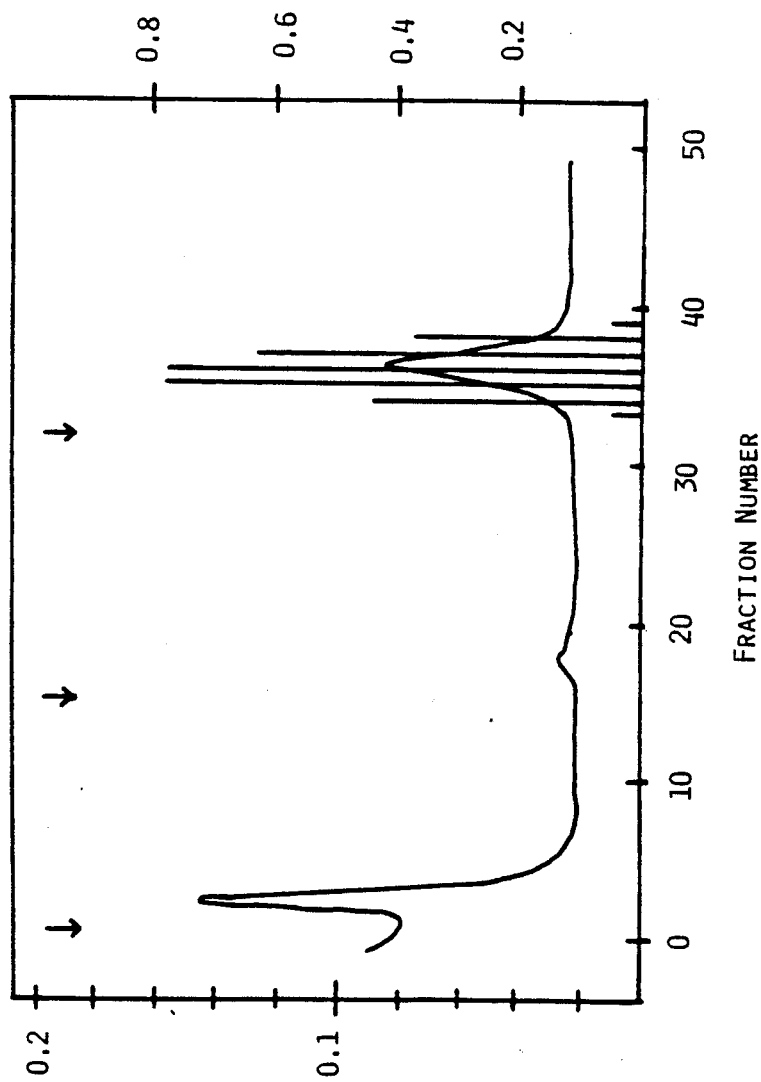

Bound plasminogen activator is eluted by washing the column with 20 mM Tris-HCl, 500 mM NaCl, 50 mM L-lysine, 0.05% Zwittergent 3-12. Approximately two volume equivalents of elution buffer are required to complete the recovery (FIG. 1B).

Alternatively, t-PA may be eluted from the column by lowering the pH. A second $Zn^{++}$-chelate Sepharose is loaded with serum-free conditioned medium and chromatographed as described above. The recovered intact t-PA (Zn B) is diluted and loaded onto a lysine-Sepharose column. This column is washed at 4° C. with 10 mM Tris pH 8.0, 500 mM NaCl, 0.01% Pluronic F-68 until the absorbance of the eluent buffer is equal to the applied buffer. The lysine-Sepharose column is washed with 3-4 column volumes of 3 mM glutamic acid pH 8.0, 160 mM NaCl, 0.01% Pluronic F-68. Bound plasminogen activator is eluted with 3 mM glutamic acid pH 4.0 160 mM NaCl, 0.01% Pluronic F-68. In our example, the t-PA concentration was 0.2-0.3 mg/ml and the pH of the eluent was 4.4±0.1 (FIG: 1C).

This eluted t-PA was concentrated up to 1 mg/ml over an Amicon YM-30 ™ membrane by pressure dialysis. To avoid nonspecific binding of plasminogen activator, the membrane was pretreated with 3 mM glutamic acid pH 4.0, 160 mM NaCl, 0.01% Pluronic F-68.

After concentration, the t-PA solution was brought up to an Pluronic F-68 concentration of 0.1%. Five mg of mannitol was added per ml. This solution was lyophilized and reconstituted by the addition of water without any loss of activity.

The purification t-PA from serum-supplemented and serum-free media was in excess of 75%. The recovered t-PA, when analyzed by gel electrophoresis under non-reducing conditions (Laemmli, supra) had an apparent molecular weight of about 66,000 Daltons and represented greater than 99% of the total protein (FIG. 2). This t-PA exists primarily as the one-chain form as evidenced by absence of 32,000 and 34,000 subunits of two-chain seen under reducing conditions (FIG. 2). The enzymatic, physiochemical and antigenic properties of the recovered protein confirmed that the material was tissue plasminogen activator. Amino acid sequencing (Applied Biosystems Model 470A Sequencer) indicated the presence of two molecular forms with N-terminal sequences shown in Table 1. The sequences and the N-terminal heterogeneity are as reported in the literature. (Wallen et al., Eur. J. Biochem 132:681–686 [1983]; Pohl et al., Biochemistry 23:3701–3707 [1984]).

When the procedures described above are used, 5-25% of the total t-PA is in the form of degraded t-PA, and therefore recovered in the "Zn A" eluate. If liquid medium containing serum, which has not been preadsorbed with lysine-Sepharose was used, 25–100% of total enzyme eluted from the Zn-chelate column is found in the Zn A eluate. Zymographic analysis (Granelli-Piperno & Reich, supra) of typical "Zn A" and "Zn B" pools are shown in FIG. 3 and demonstrated the separation of low molecular weight form of t- PA from the bulk of the intact t-PA.

| Cycle No. | Major Peak | Minor Peak | Predicted Sequence |
|---|---|---|---|
| 1 | Gly | — | Gly |
| 2 | Ala | — | Ala |
| 3 | Arg | — | Arg |
| 4 | Ser | Ser | *Ser |
| 5 | Tyr | Tyr | Tyr |
| 6 | Gln | Gln | Gln |
| 7 | Val | Val | Val |
| 8 | Ile | Ile | Ile |
| 9 | — | Cys | Cys |
| 10 | Arg | Arg | Arg |
| 11 | Asp | Asp | Asp |
| 12 | Glu | Glu | Glu |
| 13 | Lys | Lys | Lys |
| 14 | Thr | Thr | Thr |
| 15 | Gln | Gln | Gln |
| 16 | Met | Met | Met |
| 17 | Ile | Ile | Ile |
| 18 | Tyr | Tyr | Tyr |
| 19 | Gln | Gln | Gln |
| 20 | — | — | Gln |
|  | His | His |  |
|  | Gln | Gln |  |
|  | Ser | Ser |  |

EXAMPLE II:

Removal of Degraded t-PA from Recovered t-PA.

The t-PA recovered from conditioned media which has been supplemented with 0.5% serum. The conditioned medium was applied to $Zn^{++}$ chelate Sepharose and the t-PA recovered using the protocol taught in the literature (Rijken et al., supra, Rijken & Collen, supra).

The recovered t-PA, containing intact and degraded enzyme, was then chromatographed on lysine-Sepharose as described above. This preparation of t-PA, which contained approximately equal amounts of intact and degraded t-PA, and which was contaminated with other unrelated proteins, was dialyzed against 20 mM Tris-HCl (pH 8.5), 1.0 M NaCl, 0.01% Tween 80, or other buffers appropriate for the binding of t-PA to Zn- chelating Sepharose resin. This material (FIG. 4, "Load") was applied to a column of the resin, and washed and eluted as described in Example I. As expected, the majority of degraded t-PA was eluted from the column in the "Zn A" fraction (FIG. 4) whereas the intact t-PA now substantially free of the 50,000 mw form was recovered in the "Zn B" fraction (FIG. 4).

EXAMPLE III:

Recovery of t-PA from E. coli Extracts.

A guanidine-HCl extract of E. coli expressing pre-pro-t-PA was prepared as described previously (Pennica et al., Nature 301:214–221 [1983]). The extract was diluted to a concentration of 1 M in guanidine-HCl with 20 mM Tris-HCl (pH 7.5), 0.01 M NaCl, 0.01% Tween 80 and loaded onto the $Zn^{++}$ chelate Sepharose column. Chromatography on the $Zn^{++}$ chelate and lysine Sepharose columns proceeded as described in Example I with the intact E. coli t-PA activity eluting as expected for intact mammalian cell enzyme.

EXAMPLE IV:

Effect of pH on the Solubility of t-PA.

Aliquots of a solution of intact t-PA at a concentration of approximately 0.1 mg/ml were dialyzed to equilibrium against 10 mM buffers of several pH values containing 160 mM NaCl and 0.1% Tween 80. Each sample was transferred to a centrifuge tube, mixed thoroughly and an aliquot was assayed on a plasminogen enriched fibrin plate as described in Example 4. The sample was centrifuged at 16,000 g to sediment insoluble material. The t-PA activity remaining in the supernatant fractions was assayed on fibrin plates. Prior to centrifugation each sample was shown to contain the same amount of t-PA; however, in those samples with pH values greater than pH 5 and up to at least pH 10.5 a substantial fraction of the t-PA was contained in aggregates which could be removed by centrifugation (Table 2). T- PA activity was determined using zonal clearing on plasminogen-enriched fibrin plates (Haverkatet & Brakman, Prog. in. Chem. Fibrin. Thromb. 1:151–159 [1975]) and was measured relative to a standardized preparation of t-PA.

TABLE 2

Solubility of t-PA at various pH values. The t-PA remaining in solution after centrifugation of the samples was determined on fibrin plates. All samples prior to centrifugation contained approximately 46,000 units/ml.

| pH | Soluble t-PA (units/ml) |
|---|---|
| 4.0 | 46,000 |
| 5.0 | 46,000 |
| 6.0 | 34,000 |
| 7.8 | 8,500 |
| 9.3 | 15,500 |
| 10.5 | 34,000 |

This experiment demonstrates that at neutral pH values t-PA aggregates even in relatively dilute solutions. Therefore, to concentrate t-PA for use in a pharmaceutical formulation, weakly buffered solutions of acidic pH should be employed.

EXAMPLE V:

Comparison of Adsorbent Substrates.

Chromatographic resins were synthesized by dissolving approximately one millimole of each of several diaminocarboxylic acids in one ml of 0.1 M sodium bicarbonate. Each acid was added to 3 ml of a 66% slurry of CNBr-activated Sepharose or activated CH-Sepharose in water. Solutions were mixed with gentle agitation of 20 minutes at 4° C.

The coupling reactions were terminated by the addition of 200 ml of triethanolamine. After an additional 30 minutes of agitation at 4° C., the substrates were washed as suggested by the manufacturer of the Sepharose.

One-half of each packed resin was transferred to a small column and washed with 5 ml of 20 mM Tris-HCl, pH 8.0, 0.1% Tween 80. t-PA samples containing 2000 units in 5 ml of the same buffer were passed over each column. Each adsorbent substrate was washed with 5 ml of the same buffer. Thereafter, t-PA was eluted with 20 mM Tris-HCl (pH 8.0), 0.25 M NaCl, 0.2 mM e-aminocaprioic acid, 0.1 Tween 80. The enzyme activity recovered thereby was measured on plasminogen enriched fibrin plates (Haverkatet & Brakman, supra) to calculate the fraction of enzyme bound by the adsorbent. The results, as shown in Table 3 below, demonstrated that L- lysine provides the best chromatographic ligand and that a six carbon spacer between the solid support and the ligand improved the efficiency of t-PA binding.

TABLE 3

| Binding of t-PA to Immobilized Diaminocarboxylic Acids | | |
|---|---|---|
| | t-PA Units Bound | |
| Immobilized Ligand | CH-Sepharose | Sepharose |
| 2,3-diaminopropionic acid | 11 | 4 |
| D,L-orinithine | 16 | 4 |
| D-lysine | 360 | 64 |
| L-lysine | 1,040 | 780 |
| 2,4-diaminobutyric acid | 80 | 56 |
| diaminopimelic acid | 180 | 4 |

EXAMPLE VI:

The Use of Cation Exchange Chromatography for the Concentration of t-PA.

The experiments described in Example IV demonstrate that t-PA is maximally soluble at acidic pH. The isoelectric point of t-PA is approximately pH 7.5 to 8, therefore in acidic solutions t-PA should possess a net positive charge and bind to cation exchange resins such as SP-Sepharose or S- Sepharose-FF. These cation exchangers typically will reversibly bind 10 to 100 mg of protein per ml of resin, and thus provide a matrix for the concentration of t-PA.

One ml of S-Sepharose Fas Flot ™ was equilibrated with 0.01 M sodium acetate, 150 mM NaCl, 0.01% Tween 80, 0.02% sodium azide at pH 4.5 and then packed into a 0.5 cm (i.d.) column. Five mg of t-PA in 150 ml of 3 mM glutamic acid, 160 mM NaCl, 0.01% Pluronic F-68, pH 4.0 was applied to the resin at approximately 50 ml $h^{-1}$.

The column was washed at 12 ml h$^{-1}$ with 2.5 mM sodium citrate, 100 mM NaCl, 0.1% Pluronic F-68, pH 5.0 until the adsorbancy at 280 nM of the effluent equalled that of the solution applied to the column. The column was eluted at 12 ml hr$^{h-1}$ with 2.5 mM sodium citrate, 1 M NaCl, 0.07 Pluronic F-68 at pH 5.0. Fractions, typically 1/4 column volume were collected and aliquots were assayed for t-PA activity (Table 4).

TABLE 4

Recovery of t-PA from S-Sepharose fast flow.
t-PA activity was assayed as described in Example 4.

| Sample | Volume (ml) | t-pA (I.U.) | Recovery (%) |
|---|---|---|---|
| t-PA load S-Sepharose FF | 150 | 3,000,000 | 100 |
| Flow through | 5 | 500 | 0 |
| Peak fractions | 8.5 | 3,500,000 | 115 |

The product was concentrated by a factor of 20 to a final concentration of 0.65 mg/ml with full recovery of activity. This t-PA solution was dialyzed to equilibrium without loss of activity against a solution containing 3 mM glutamic acid, 160 mM NaCl and 0.01% Pluronic F-68 (pH 4.0). This solution is suitable for further concentration by ultrafiltration or direct formulation in a pharmaceutical preparation.

EXAMPLE VII:

The Effect of Aprotinin on Yield of One-Chain t-PA from Various Tissue Culture Media.

Aprotinin is known to inhibit the conversion of one-chain t-PA into two- chain t-PA (Rijken & Collen, supra). The concentration of aprotinin necessary to optimize recovery of one-chain t-PA relative to two-chain degraded forms of t-PA was determined. A genetically engineered strain of CHL-1 cells was grown to confluency in a 24 well plate in a medium composed of a 1:1 mixture of Ham's F- 12 and DMEM (F-12/DMEM) supplemented with 0.5% heat-inactivated fetal bovine serum which had been pre-treated with lysine-Sepharose, or medium supplemented with 0.5% heat-activated fetal bovine serum was added to the cells. Aprotinin was added to each of the media so that individual wells in the tissue culture plates contained 0, 1, 5, 10, 50 or 100 KIU of aprotinin/ml. The plates were incubated at 37° C. for 48 hours.

The media were harvested, clarified by centrifugation and assayed for t-PA activities. The total t-PA in each sample was determined from the diameter of the zone of clearing effected by a 5 ul sample placed into a well formed in a plasminogen enriched fibrin plate (Haverkatet & Brakman, supra). Neither the choice of medium nor concentration of aprotinin had any effect on total t-PA production. Each sample contained approximately 900 I.U. t-PA per milliliter.

The effect of aprotinin and medium on the conversion of one-chain t-PA to the two-chain form was determined by Western blot analysis (Burnette, Anal. Biochem. 112:;195 [1981]). The protein from one ml of each sample of the conditioned media was recovered by precipitation with trichloroacetic acid (10% final concentration). The pellet of protein obtained by centrifuging the samples for 10 minutes at 15,000 g was resolubilized in 20 μl of sample buffer (Laemmli, supra). The samples, which contained 10 mM dithiothreitol, were boiled for 7 minutes, then loaded onto an 8.75% polyacrylamide gel. After running the dye front to the bottom, the proteins were electroblotted onto nitrocellulose.

Figure 5A:
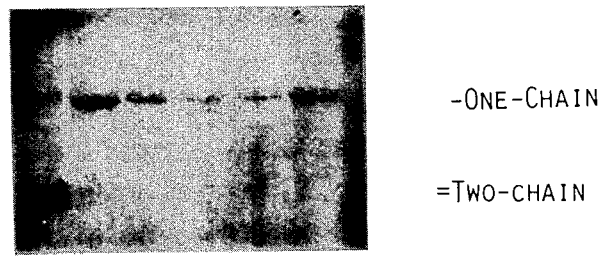
FIG. 5 shows the inhibition by aprotinin of the conversion of one-chain to two-chain t-PA in various tissue culture media. Increasing amounts of aprotinin were added to tissue culture media used for the production of t-PA. The t-PA synthesized during 48 hours of incubation were analyzed by "Western Blot" analysis as described in the text. A shows t-PA produced in serum-free medium; B, medium supplemented with 0.5% serum, and C, medium supplemented with 0.5% serum which had been pre-adsorbed with lysine Sepharose.
Figure 5B:
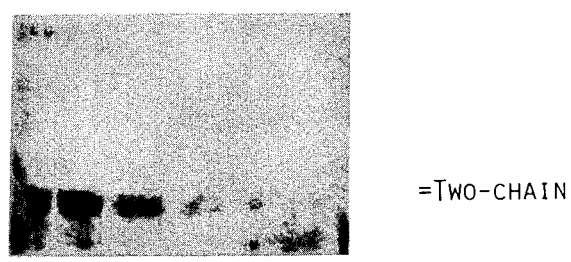

The nitrocellulose was incubated in 5% BSA in 10 mM Tris-HCl pH 7.5, 0.9% NaCl for 30 minutes at room temperature, and then incubated with antiserum to denatured human t-PA (10 microliters serum in 10 ml of 10 mM Tris-HCl pH 7.5, 0.9% NaCl 3% BSA, 0.05% Tween 20) overnight at 4° C. The binding of the rabbit anti-t-PA was detected using the Vectastain ABC$^{TM}$ (avidin-biotin-horseradish peroxidase complex) kit and 4-chloro-1-napthol as the substrate for the peroxidase (FIG. 5). On the blots, one-chain t-PA is seen as a band at approximately 66,000 mw, while the subunits of the two-chain enzyme are detected as bands at 32,000 and 34,000 mw. In those experiments wherein serum was used no single-chain t-PA can be visualized. In control experiments this was shown to be the result of the large amount of albumin in the sample which both distorts the single-chain t-PA band during the gel electrophoresis and further inhibits the complete binding of proteins in this molecular weight range to the nitrocellulose. However, the presence of serum had no effect on the migration or transfer of the two-chain bands.

Figure 5C:
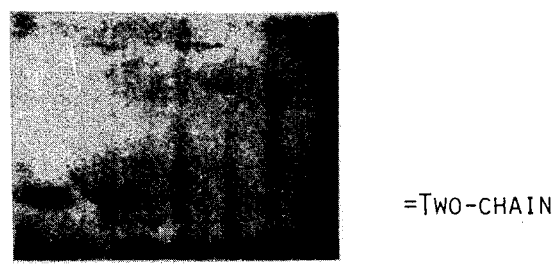

Complete inhibition of the conversion of one-chain t-PA to two-chain was observed at 5-10 KIU/ml aprotinin for either serum-free medium (FIG. 5) or medium containing 0.5% "scrubbed serum" (FIG. 5C). When "non-scrubbed" serum was used even 100 KIU aprotinin per ml was not adequate to completely inhibit formation of two-chain t-PA.

In media containing serum, the conversion of one-chain t-PA to two-chain t-PA is a result of proteolytic activities involving t-PA as a substrate. These activities will additionally cause degradation of t-PA. Eliminating or blocking the activity which causes degradation of t-PA is an important step in maintaining the integrity of t-PA in conditioned medium.

EXAMPLE VIII:

The stimulation of "intact" and "degraded" t-PA by fibrinogen fragments.

A striking difference between tissue plasminogen activators and urokinase is that the former adsorb to fibrin (Thorsen et al, supra), which results in a marked enhancement of the activation of plasminogen (Wallen, Prog. Chem. Fibrinolysis Thrombolysis 3:167–181 (1978). Fragments generated from a CNBr cleavage of fibrinogen (Niewenhuizen et al, Biochim. Biophys. Acta. 755:531–533 (1983)) also stimulate the process of plasminogen activation by t-PA.

Twenty μl of t-PA solutions each containing 0.2 units of one-chain, two-chain or degraded (50,000 mw) t-PA as measured by fibrin plate assay, was added to 180 μl of solution containing plasminogen, the chromogenic substrate S-2251 (Helana Labs, Beaumont, TX from Kabi Laboratories), and with or without fibrinogen fragments (Niewenhuizen et al, supra). In this assay (Wiman et al, Biochim. Biophys. Acta 579:142–154, 1979) t-PA cleaves plasminogen to form active plasmin. The resulting plasmin activity is assayed using the chromogenic substrate S-2251, which yields a yellow color, upon hydrolysis by plasmin. The mixture (0.2 units t-PA, 0.2 mM S-2251, 20 mg/ml CNBr-fragments of human fibrinogen) was incubated at 37° and the absorbance change at 405 nm was read at 15-minute intervals. Activity is determined from a plot of adsorbance vs (time)² which is linear (Drapier et al, Biochimie 61:463–571 (1979)).

As is shown in Table 5 equivalent amounts of t-PA, as defined by equal zones of clearing on a fibrin plate, exhibited very different activities in the S-2251 assay. In the absence of fibrinogen fragments, two-chain t-PA was much more active than either one-chain or degraded t-PA. The addition of fibrinogen fragments greatly stimulated the activity of the one-chain enzyme and to a lesser extent that of the two-chain form such that the resulting activities were equivalent. The degraded (50,000 mw) t-PA was stimulated much less by the fibrinogen fragments.

These data suggest that the best form of t-PA for therapeutic applications is the one-chain enzyme as its activity is much more fibrin-specific than that of the two-chain form. Both forms of the intact enzyme are much more fibrin-specific than the degraded t-PA.

TABLE 5

| | Stimulation of t-PA by fibrinogen fragments (FF) | | |
|---|---|---|---|
| Enzyme | Activity −FF | ($A_{405}/min^2 \times 10^5$) +FF | Fold Stimulation |
| One-chain | 0.06 | 14.8 | 250 |
| Two-chain | 0.34 | 16.3 | 48 |
| Degraded (50,000 mw) | 0.08 | 1.5 | 19 |

EXAMPLE IX:

Purification of t-PA from Conditioned Liquid Medium using urea.

Liquid medium (1:1 mixture Ham's F-12 and DMEM) containing 0.5% fetal bovine serum, which had been pre- adsorbed with lysine-Sepharose, and 10 KIU aprotinin per ml was conditioned by incubation with RPMI 7932 cells (Rijken and Collen, supra; Kluft et al., supra), or alternatively, other plasminogen activator producing cells.

This conditioned liquid medium was clarified from cells and cellular debris by microfiltration using a Prostak unit with a 0.45 micron filter.

Clarified medium is passed through a 0.2 micron filter, adjusted to approximately pH 7.2 to 7.4 with NaOH, chilled to 4° C., and passed through a chelating Sepharose column complexed with $Zn^{++}$ as recommended by the manufacturer (Pharmacia, Inc.). In a typical chromatographic run, 600 liters of clarified media containing t-PA at a concentration of 10 mg/ml are introduced onto 3.5 l of resin. The column was previously equilibrated with phosphate buffered saline. Up to 200 equivalent column volumes of medium are passed through the resin at rates up to 50 cm per hour for a 10 cm bed of Sepharose CL-6B or 300 cm per hour for an equivalent column of Sepharose-FF. Greater than 95% of the t-PA activity will bind to the resins. The column is next washed at a rate of 6 liters per hour with probes monitoring pH, conductivity and optical density. The column is first washed with 20 mM Tris-HCl pH 8.0, 1.0 M NaCl, 0.01% Tween 80, 10 KIU aprotinin per ml followed by 20 mM Tris-HCl (pH 8.0), 25 mM NaCl, 0.01% Tween 80, 10 KIU aprotinin per ml. The column was then washed with the previous buffer plus 0.1M imidazole which elutes off the degraded forms of t-PA, about 5% of the intact t-PA and most of the non-t-PA protein bound to the column. The remaining intact enzyme is recovered by passing 10 mM Tris-HCl (pH 8.0), 0.5 M NaCl, 50 mM Na EDTA, 0.01% Tween 80, 2.0 M urea and 10 KIU Aprotonin/ml at 4° C. through the resin. The column effluent is collected. This fraction is typically 50–60% pure.

The partially purified product is next diluted 5-fold with a buffer consisting of 10 mM citrate, 0.05% tween 80, and 2M urea at pH 4.7 and the final mixture is adjusted to pH 4.85. This material is pumped a DEAE resin which has been preequilibrated with 0.01% Tween 80, 0.1 M NaCl, 10 mM sodium citrate and 2M urea at pH 5.0. The DEAE effluent is adjusted to pH 8.0 with NaOH and ethylene glycol is added to a final concentration of 10%.

The resultant pre-lysine t-PA solution (approximately 30 liters) is loaded onto a 2 liter lysine column which has been pre-equilibrated with a buffer of 10 mM Tris, 0.1 M NaCl 0.01% Tween 80, 2M urea, pH 7.6 at 4° C. The lysine resin of choice has an extended arm and is derived from coupling of lysine to activated CH-Sepharose 4B.

For elution, the column is washed with 10 mM Tris, 0.5 M NaCl, 0.05% Tween 80, 10% ethylene glycol (100 gm in 1 L), pH 8.0 at 4.C, followed by 10 mM Tris, 0.1 M NaCl, pH 7.6 at 4° C. The t-PA is eluted with 100 mM glycine-HCl, pH 3.0 at 4° C.

The t-PA can be ultrafiltered and concentrated to 20 mg/ml of t-PA in 30 mM glycine-HCl at pH 3.0.

Optionally the t-PA preparation can be passed through an exclusion column such as G-100 prior to sterile filtration.

EXAMPLE X:

Comparative properties of t-PA produced from genetically altered human cells (CHL-1) and t-PA produced from genetically altered CHO cells.

For the following analyses, human t-PA (mt-PA) was produced by melanoma cells of human origin containing the t-PA containing plasmid found in E. coli culture ATCC Acess. No. 67,443. T-PA derived from CHO cells (Activase) is commercially available from Genentech, Inc. (South San Francisco, CA). Physiochemical and biological comparisons were made with the following results:

A. Purity and Homogeniety

Using standard techniques of electrophoresis and chromatography, the mt-PA produced by the disclosed methods contains no detectable levels of unrelated proteins or degraded t-PA fragments. The composition migrates in columns and gels as a substantially single peak or band. Relatively higher levels of undefined protein contaminants are found in Activase.

The mt-PA produced by the methods described herein provide for a composition of t-PA that has a percent of one-chain form that ranges from 98% to 90% with a mean average of about 95% one chain present. Activase consistently demonstrated an average of 18.4% two-chain present. The chain conformations were determined by standard HPLC techniques.

T-PA has a tendency to aggregate. Direct comparison of mt-PA and Activase determined using HPLC determined that mt-PA had an aggregation of less than about .39% of the total t-PA present while Activase had about 1.42% aggregation.

B. Specific Activity

The relative specific activities for Activase and mt-PA were determined in a variety of tests including the fibrin plate analysis (Kruithof, et al., Thromb. Res. 28:251–260), the S-2288 test (Verheijen, J.H. et al., Thromb. Res. 39:281–288, 1985) and in two different plate clot analyses (Beebe, et al., Thromb. Res. 47:123–128, (1987) and Gaffney and Curtis, Thromb. and Haemos. 53:134–136, (1985) which are incorporated by reference herein).

As determined using these different assays, the mt-PA consistantly demonstrated a specific activity above 650,000 I.U/mg with assays typically giving specific activities between 700,000 and 800,000. Some testing has resulted in specific activities in excess of 900,000 I.U./mg up to 1,100,000 I.U./mg. It is thought that the levels of purity and homogeniety achieved using the methods of this invention are reaching the theoretical limits of purity that are commercially practical for formulations of human pharmaceuticals. Under the independent testing, Activase had a specific activity of 585,556 I.U./mg and mt-PA had a specific activity of about 750,000 I.U./mg.

From active site titrations it was determined that Activase has only 88% of the number of active sites in mt-PA. This indicates that 12% of the Activase molecules are inactive compared to the mt-PA on a mole to mole basis.

C. Glycosylation

Using several independent methods, carbohydrate analysis showed that the sialic acid content of Activase was substantially higher than that determined for mt-PA. Specifically, using HPLC methodology, it was determined that the percent sialic acid per mole of t-PA was 1.52 for Activase and only 0.48 for mt-PA. Alternatively, using a colorimetric assay with thiobarbituric acid (Warren, L.J. J. Biol. Chem. 234:1971, 1959), the percent sialic acid / mole of t-PA formed was 1.96 for Activase and 0.41 for mt-PA. These results point to fundamental differences in the oligosaccharide processing between the two cell lines and demonstrate fundamental chemical differences between the two compositions.

D. Stability

The described formulations of mt-PA are inherently more stable as a result of their being stored in acidic buffers and a result of their containing substantially less two-chain form in the initial composition than Activase.

Although the foregoing invention has been described in some detail by way of illustration and example for purposes of clarity of understanding, it will be obvious that certain changes and modifications may be practiced within the scope of the appended claims. However, it must be stressed that the production of intact t-PA which is suitable for subsequent formulation in pharmaceutical compositions requires following the essential steps described in the foregoing invention.

Each and every of the references, both academic and patent related, cited throughout this document are hereby incorporated by reference.

What is claimed is:

1. A method for recovering intact tissue plasminogen activator (t-PA) form a liquid medium containing said intact t-PA and at least one of degraded t-PA and unrelated proteins comprising the steps of:
   (a) contacting said liquid medium with a metal chelate adsorbent substrate selected from divalent cation chelates;
   (b) subjecting said metal chelate adsorbent substrate to a first solution which selectively dissociates therefrom degraded t-PA but not said intact t-PA; and
   (c) subjecting said metal chelate adsorbent of step b to at least one second solution which selectively dissociates therefrom the intact t-PA.

2. A method according to claim 1 wherein the second solution comprises a chaotropic agent.

3. The method of claim 2 wherein the choatropic agent is urea at a molar concentration of between about 1.0 and 3.0.

4. The method of claim 1 wherein the liquid medium comprises intact t-PA at a concentration of about 0.01 to 15.0 mg/ml.

5. The method as recited in claim 1 wherein said first solution comprises a low ionic strength solution having a salt concentration in the range of about 25 millimolar to 100 millimolar and said second solution comprises a high ionic strength solution having a salt concentration in the range of about 100 millimolar to 4 molar.

6. The method as recited in claim 5 wherein said salt is sodium chloride.

7. The method as recited in claim 6 wherein said first solution comprises about 25 mM sodium chloride and said second solution comprises about 1 molar sodium chloride.

8. The method as recited in claim 1 wherein said first solution further comprises at least one first disrupting agent capable of selectively disrupting the interaction between said degraded t-PA and said metal chelate adsorbent.

9. The method as recited in claim 1 wherein said second solution further comprises at least one second disrupting agent capable of selectively disrupting the interaction between said intact t-PA and said metal chelate adsorbent.

10. The method as recited in claim 8 wherein said first disrupting agent comprises about 25–250 mM imidazole.

11. The method as recited in claim 8 wherein said first solution comprises about 25 mM sodium chloride and about 100 mM imidazole.

12. The method as recited in claim 9 wherein said second disrupting agent is selected from the group consisting of imidazole, zinc, ethylenediaminetetraacetic acid and salts thereof.

13. The method as recited in claim 12 wherein said second disrupting agent comprises about 10–250 mM sodium ethylenediaminetetraacetic acid.

14. The method as recited in claim 9 wherein said second solution comprises about 1 molar sodium chloride and about 50 mM sodium ethylenediaminetetraacetic acid.

15. The method as recited in claim 1 wherein said metal chelate adsorbent substrate comprises molecules having a anionic ligand able to chelate metal ions.

16. The method as recited in claim 15 wherein said anionic ligand is a dicarboxylic acid.

17. The method as recited in claim 15 wherein said metal is zinc.

18. The method as recited in claim 1 further comprising concentrating said intact t-PA after step C.

19. The method of claim 18 wherein said intact t-PA is concentrated in the presence of non-ionic or zwitterionic detergent.

20. The method of claim 19 wherein said intact t-PA is concentrated by lyophilization in the presence of at least one stabilizing agent.

21. The method of claim 20 wherein said stabilizing agent is mannitol.

22. A method for recovering intact tissue plasminogen activator (t-PA) from a cell culture medium comprising the steps of:
   (a) providing a liquid medium selected from the group consisting of serum-free medium, serum-supplemented medium, serum-fraction supplemented medium and albumin-supplemented medium;
   (b) pretreating said serum-supplemented or serum fraction supplemented medium with a first adsorbent substrate capable of removing substantially all plasminogen-like contaminants present in the serum-supplemented or serum-fractions supplemented medium;
   (c) adding to said liquid medium a plasmin inhibitor;
   (d) contacting said liquid medium with a metal chelate adsorbent substrate selected from divalent cation chelates;
   (e) subjecting said metal chelate adsorbent substrate to a first solution which selectively dissociates therefrom degraded t-PA but not said intact to-PA;
   (f) subjecting said metal chelate adsorbent of step e to at least one second solution which selectively dissociates therefrom the intact t-PA;
   (g) contacting the intact t-PA-containing solution eluted in step with A with a substrate comprising an immobilized aminocarboxylic acid;
   (h) subjecting said immobilized aminocarboxylic acid substrate to at least, one third solution that dissociates from said substrate other containing proteins but not said intact t-PA; and
   (i) subjecting said immobilized aminocarboxylic acid substrate of step h to at least one fourth solution that dissociates from said substrate said intact t-PA.

23. A method according to claim 22 wherein the second solution comprises about 0.5 to 3.5 M urea.

24. The method of claim 23 wherein the molar concentration of urea is about 1.0 to 3.0 M.

25. The method of claim 22 wherein the first adsorbent substrate comprises an aminocarboxylic acid.

26. The method of claim 25 wherein the aminocarboxylic acid is L-lysine.

27. The method as recited in claim 22 further comprising concentrating said intact t-PA.

28. The method of claim 27 wherein said intact t-PA is concentrated in the presence of non-ionic or zwitterionic detergent.

29. The method of claim 28 wherein said intact t-PA is concentrated by lyophilization in the presence of at least one stabilizing agent.

30. The method of claim 29 wherein said stabilizing agent is mannitol.

31. A biologically active compound produced by the method of claim 6 or 22 comprising intact t-PA substantially free from degraded t-PA.

32. A composition having thrombolytic activity comprising intact t-PA substantially free from degraded t-PA proteins and unrelated proteins.

33. A composition of claim 32 comprising intact one-chain t-PA substantially free from two-chain t-PA and degraded t-PA.

34. A composition of claim 33 wherein the percent one-chain form of t-PA is about or in excess of 90% (w/w) of the total t-PA.

35. A composition of claim 34 wherein the specific activity is between about 700,000 and approximately 800,000 international units per milligram.

36. A composition of claim 34 wherein the composition is substantially free of detergent.

37. A composition of claim 33 wherein the t-PA is substantially in a nonaggregated form.

38. A composition of claim 37 wherein the nonaggregated form of t-PA is at least about 99% of the total t-PA.

39. A composition of claim 32 having a sialic acid content less than about 1.0% of the total composition by weight.

40. A composition of intact one-chain t-PA substantially free of degraded t-PA and having a specific activity approximately at or in excess of 650,000 international units per milligram.

41. A composition of claim 40 wherein the percent one-chain t-PA is at least about 95% (w/w) of the total t-PA.

42. A composition of claim 40 wherein the t-PA is a t-PA free of non-human eukaryote proteins.

43. A composition of claim 42 having a sialic acid content less than about 0.5% of the total composition by weight.

44. A composition of claim 40 wherein the t-PA is substantially free of detergent.

45. A composition comprising t-PA that is characterized by a specific activity above about 700,000 international units per milligram; that is substantially free of detergent; that is composed of one-chain t-PA in excess of about 95% (w/w) of the total t-PA; that is substantially free of non-human proteins and proteins not related to t-PA; that is composed of sialic acid that is less than about 0.5% of the total composition by weight; and that is substantially free of degraded t-PA.

46. A method of treating a host in need of thrombolytic therapy comprising administering to said host an effective amount of the composition of any of claim 31 or 32.

* * * * *

UNITED STATES PATENT AND TRADEMARK OFFICE
CERTIFICATE OF CORRECTION

PATENT NO. : 4,960,702
DATED : October 2, 1990
INVENTOR(S) : Rice et al.

It is certified that error appears in the above-identified patent and that said Letters Patent is hereby corrected as shown below:

In column 2, line 32, delete " Deq- " and substitute therefor, -- Deg- --;

In column 5, line 24, delete "thereof Especially" and substitute therefor, --thereof. Especially--;

In column 10, line 36, delete "Adsorbinq" and substitute therefor, --Adsorbing--;

In column 11, line 65, delete "Banvai" and substitute therefor, --Banyai--;

In column 16, line 59, delete "osmolaritycryoprotectants" and substitute therefor, --osmolarity-cryoprotectants--;

In column 20, line 37, insert the Table legend as follows:

--Table 1: Amino-terminal sequence of t-PA.
Purified protein was subjected to automated sequence analysis on an Applied Biosystems Model 470A Protein Sequencer. At each cycle two amino acids present in a ratio of 3:2 were detected. These data yielded two sequences which differed by the presence or absence of three residues. (*) indicates the reported alternative amino terminus.--;

UNITED STATES PATENT AND TRADEMARK OFFICE
CERTIFICATE OF CORRECTION

PATENT NO. : 4,960,702
DATED : October 2, 1990
INVENTOR(S) : Rice et al.

It is certified that error appears in the above-identified patent and that said Letters Patent is hereby corrected as shown below:

In column 24, line 68, and continuing to column 25, line 1, delete "(ti-me)$^2$" and substitute therefor, --(time)$^2$--;

In column 26, line 22, delete "4.C" and substitute therefor, --4° C--;

Column 27, claim 1, line 59, delete "form" and substitute therefor, --from--;

Column 29, claim 22, line 26, delete "eluted in step with A" and substitute therefor, --eluted in step f--; and In claim 22, line 30, delete "containing" and substitute therefor, --contaminating--.

Signed and Sealed this

Twelfth Day of May, 1992

*Attest:*

DOUGLAS B. COMER

*Attesting Officer*   *Acting Commissioner of Patents and Trademarks*